United States Patent
Rekik

(10) Patent No.: US 9,730,949 B2
(45) Date of Patent: Aug. 15, 2017

(54) ANGIOTENSIN CONVERTING ENZYME INHIBITORS FOR TREATING OPTIC NEUROPATHY OR CONGENITAL OPTIC ATROPHY

(71) Applicant: Raouf Rekik, Montplaisir-Tunis (TN)

(72) Inventor: Raouf Rekik, Montplaisir-Tunis (TN)

( * ) Notice: Subject to any disclaimer, the term of this patent is extended or adjusted under 35 U.S.C. 154(b) by 0 days.

(21) Appl. No.: 14/411,641

(22) PCT Filed: Jun. 28, 2013

(86) PCT No.: PCT/IB2013/001375
§ 371 (c)(1),
(2) Date: Dec. 29, 2014

(87) PCT Pub. No.: WO2014/001889
PCT Pub. Date: Jan. 3, 2014

(65) Prior Publication Data
US 2015/0174146 A1    Jun. 25, 2015

(30) Foreign Application Priority Data

Jun. 29, 2012 (TN) .............................. TN 2012/0343

(51) Int. Cl.
| | |
|---|---|
| *A61K 31/675* | (2006.01) |
| *A61K 9/00* | (2006.01) |
| *A61K 31/40* | (2006.01) |
| *A61K 31/55* | (2006.01) |
| *A61K 31/403* | (2006.01) |
| *A61K 31/472* | (2006.01) |
| *A61K 31/401* | (2006.01) |

(52) U.S. Cl.
CPC .......... *A61K 31/675* (2013.01); *A61K 9/0048* (2013.01); *A61K 31/40* (2013.01); *A61K 31/401* (2013.01); *A61K 31/403* (2013.01); *A61K 31/472* (2013.01); *A61K 31/55* (2013.01)

(58) Field of Classification Search
CPC ...... A61K 31/55; A61K 31/40; A61K 31/472; A61K 31/675; A61K 31/403; A61K 9/0048
USPC ............................................................ 514/91
See application file for complete search history.

(56) References Cited

U.S. PATENT DOCUMENTS

| 4,656,188 A | 4/1987 | Veber et al. |
| 7,049,340 B1 | 5/2006 | Rekik |
| 2010/0273894 A1 | 10/2010 | Miller |

FOREIGN PATENT DOCUMENTS

| FR | 2826276 | 12/2002 |
| JP | 2013527222 | 6/2013 |
| WO | 2011/151685 | 12/2011 |

OTHER PUBLICATIONS

Ryu, Samuel, et al., "Mitigation of radiation-induced optic neuropathy in rats by ACE inhibitor ramipril: importance of ramipril dose and treatment time;" J. Nuerooncol, 2007, vol. 82, pp. 119-124.
Detry-Morel, M., "Perspectives dans le traitement médical de la neuropathie glaucomateuse—Bases de la neuroprotection," J. Fr. Ophtalmol., 1999; vol. 22, No. 1, pp. 122-134, with English translation.
Wong, Tien, et al., "The eye in hypertension," www.thelancet.com, 2007, vol. 369, pp. 425-435.

*Primary Examiner* — Kristin Vajda
(74) *Attorney, Agent, or Firm* — Duane Morris LLP; Gregory M. Lefkowitz

(57) ABSTRACT

The present invention relates to an ophthalmic composition comprising at least one angiotensin converting enzyme (ACE) inhibitor and a pharmaceutically acceptable vehicle for use as an ophthalmic neuroprotector in treating an optic neuropathy or congenital optic atrophy.

13 Claims, 7 Drawing Sheets

ANGIOTENSIN CONVERTING ENZYME INHIBITORS FOR TREATING OPTIC NEUROPATHY OR CONGENITAL OPTIC ATROPHY

CROSS-REFERENCE TO RELATED APPLICATIONS

This application is a §371 national stage entry of International Application No. PCT/IB2013/001375, filed Jun. 28, 2013, which claims priority to Tunisian Patent Application No. TN 2012/0343 filed Jun. 29, 2012, the entire contents of which an incorporated herein by reference.

FIELD OF THE INVENTION

The present invention concerns an ophthalmic composition comprising at least one angiotensin-converting enzyme (ACE) inhibitor and a pharmaceutically acceptable vehicle for use as an ophthalmic neuroprotector for treating an optic neuropathy or congenital optic atrophy. Methods for treating optic neuropathies or optic atrophies are also disclosed using the ophthalmic composition. The invention discloses, in particular, medication for the treatment of ophthalmic diseases that concern the deterioration of the optic nerve resulting in a progressive loss of vision. These ophthalmic neuroprotector compositions maintain or ameliorate the visual function such as visual acuity or visual field of the eye.

BACKGROUND OF THE PRESENT INVENTION

Optic neuropathy or, often called, optic atrophy describes the loss of some or most of the fibers of the optic nerve. The optic nerve contains axons of nerve ceils that emerge from the retina, leave the eye at the optic disc and proceed to the visual cortex where input from the eye is processed into vision. There are 1.2 million optic nerve fibers that derive from the retinal ganglion cells of the inner retina, Damage or death of the nerve cells results in loss of vision.

Optic neuropathy may be caused by ischemic optic neuropathies, optic neuritis, compressible optic neuropathies, Infiltrative optic neuropathies, traumatic optic neuropathies, mitochondrial optic neuropathies, nutritional optic neuropathies, toxic optic neuropathies and hereditary optic neuropathies. All of these different optic neuropathies are caused by various diseased states of the eye. For example, ischemic optic neuropathy is caused by insufficient blood flowing to the optic nerve, while compressive optic neuropathy Is caused by tumors, infections and Inflammatory processes that can cause lesions within the eye orbit or optic canal. Trauma to the head when exposed to direct or indirect injury can cause traumatic optic neuropathy such as blunt trauma to the forehead during an automobile accident, which can transgress the force without transgressing tissue planes.

Hereditary optic neuropathies include Leber's hereditay optic neuropathy, congenial optic atrophy and autosomal dominant optic atrophy, type Kjer, the latter of which is sometimes known as Kjer's syndrome.

Leber's Hereditary optic neuropathy otherwise known as LHON is a mitochondrially inherited degeneration of the retinal ganglion cells and their axons leading to acute or subacute loss of central vision, LHON is only transmitted through the mother and Is due to mutations in the mitochondrial genome at nucleotide positions 11778 (G->A), 3480 (G->A) and 14484 (T->C), Depending on the mutation, the degree of visual improvement does vary. For example, the 14484 mutation has a 37% to 71% chance of visual improvement, whereas the 11778 and the 3460 mutations have only a 4% chance of improvement (Stone et at, *J. Neuro-opthalamol* 12:10-4 (1992) Oostra et al, *J. Med Genet* 31:280-286 (1994)), Leber's disease is characterized by bilateral painless, subacute visual failure that develops generally in the male population during young adult life. Affected individuals are usually asymptomatic until blurring is developed in the central visual field in one eye. The other eye is affected two to three months later. Visual acuity is severely reduced to counting fingers or worse, in the majority of cases and visual field testing shows an enlarged dense central or centrocecal scotoma.

Directed therapies for mitochondrial disorders are very limited. There are general therapies involving vitamins and cofactors, folic acid, vitamin B12, thiamine, riboflavin, L-carnitine, L-arginine and creatine; electron acceptors (vitamin C and menadiol; free radical scavengers CoQ10, idebenone, alpha-lipoic acid, minocycline, cyclosporine A, glutathione and vitamin E; and inhibitors of toxic metabolites such as dichloroacetate. All of these therapies are useful, but do not aid to ameliorate or maintain vision, U.S. Patent application Serial No. 2010/0273894 A1 describes methods of treating Leber's hereditary optic neuropathy and dominant optic atrophy with tocotrienol quinones in order to alleviate the systems of the disease. Tocotrienols, as well as tocopherols are parent cozeners in the same vitamin E family and act as phenolic antioxidants. The compounds can be administered in a solid dosage form such as in tablets or in a liquid dosage form such as in solutions. The visual acuity is improved from below 20/400 to about 20/100.

Autosomal dominant optic atrophy or Kjer's syndrome is the most common type of hereditary optic neuropathies that affects optic nerves, causing reduced visual acuity and blindness. This syndrome begins in childhood and is due to mitochondrial dysfunction mediating the death of optic nerve fibers. Visual acuity is generally reduced in both eyes and severe visual loss occurs in 15% of the patients. Some patients have decreased visual acuity with age. Also patients have a generalized dyschromatopsia with blue-yellow and red-green defects. Visual fields in patient's with Kjers syndrome show central, paracentral or cecocentral scotomas.

Congenital optic atrophy is also a hereditary disease that causes degeneration or destruction of the optic nerve. The milder form of congenital optic atrophy is autosomal dominant and has a gradual onset of vision deterioration in childhood but little progression thereafter. The more severe form is autosomal recessive and is present at birth or within two years. This form is accompanied by nystagmus (involuntary eye movement). Congenital optic atrophy may also be referred to as optic nerve head pallor since a pale appearance of the optic nerve head can be seen at the back of the eye. The symptoms of this eye disease are a change in the optic disc and a decrease in visual function.

There is no known treatment for any optic neuropathy to date that is effective and aids to maintain or ameliorate visual acuity or visual field.

Thus, there is a need in the art to have an improved compositions to treat optic neuropathy and more especially, optic neuropathy caused by ischemic optic neuropathy, optic neuritis, compressible optic neuropathy, infiltrative optic neuropathy, traumatic optic neuropathy, mitochondrial optic neuropathies, nutritional optic neuropathies, toxic optic neuropathies and hereditary optic neuropathies such as Leber's, autosomal dominant optic atrophy, Kjer's disease, congenial optic atropy and inclusion of the central artery in the eye.

The present invention fulfills this need and provides ophthalmic compositions that are ophthalmic neuroprotectors to maintain or enhance visual acuity and visual field.

These and other objects are achieved by the present invention as evidenced by the summary of the invention, description of the preferred embodiments and the claims.

SUMMARY OF THE INVENTION

An ophthalmic composition comprising at least one angiotensin converting enzyme (ACE) inhibitor and a pharmaceutical acceptable vehicle for use as an ophthalmic neuroprotector in treating an optic neuropathy or congenital optic atrophy is provided by the present invention.

The at least one angiotensin converting enzyme (ACE) inhibitor used in the ophthalmic composition of the invention is fosinopril, ramipril, captopril, trandolapril, moexipril, lisinopril, quinapril, enalapril, perindopril, benazepril and mixtures thereof, as well as active metabolites thereof.

The ophthalmic composition can comprise at least one angiotensin converting enzyme (ACE) inhibitor, which is fosinoprilate, trandolaprilate, moexiprilate, ramiprilate, quinaprilate, enalaprilate, perindoprilate and benazeprilate.

The present invention further provides an ophthalmic composition comprising ramipril or ramsprilate and a pharmaceutically acceptable vehicle for use as an ophthalmic neuroprotector in treating an optic neuropathy or optic atrophy.

The optic neuropathy or optic atrophy that can be treated with the ophthalmic composition of the present invention, as described herein, can be congenital optic atrophies, ischemic optic neuropathies, inflammatory optic neuropathies, compressible optic neuropathies, infiltrative optic neuropathies, traumatic optic neuropathies, mitochondrial optic neuropathies, nutritional optic neuropathies, toxic optic neuropathies, hereditary optic neuropathies or and inclusion of the central artery in the eye.

In another aspect the present invention provides an ophthalmic composition, as described herein, that can treat hereditary optic neuropathies such as Leber's hereditary optic neuropathy, congenital optic atrophy and autosomal dominant optic atrophy, type Kjer.

In yet another aspect ischemic optic neuropathy or inflammatory optic neuropathy can be treated with the composition described herein, as well as toxic optic neuropathy due to acute methanol poisoning. With respect to the inflammatory optic neuropathy the ophthalmic composition can treat optic neuritis, neuromyelitis optica or sarcoidosis.

The ophthalmic composition, as described herein is in the form of a solid or a solution. This ophthalmic composition, as described herein, can be administered orally, parentally, intravenously, intramuscularly, topically or by infra-ocular injection. It can also be administered in the form of eye drops.

An ophthalmic composition comprising an ophthalmic composition comprising at least one angiotensin converting enzyme (ACE) inhibitor and a pharmaceutically acceptable vehicle for use as an ophthalmic neuroprotector to maintain or ameliorate the visual function the visual function of a person in need of such treatment is another aspect of the present invention.

An ophthalmic composition comprising ramipril or ramiprilate and a pharmaceutically acceptable vehicle for use as an ophthalmic neuroprotector to maintain or ameliorate the visual function the visual function of a person in need of such treatment is another aspect of the present invention.

The visual function, for example, is visual acuity or visual field.

A method for treating an optic neuropathy or optic atrophy with an ophthalmic neuroprotector said method comprising administering to the person in need of such treatment an ophthalmic composition comprising at least one angiotensin converting enzyme (ACE) inhibitor and a pharmaceutically acceptable vehicle is yet another aspect of the invention described herein.

A method for treating an optic neuropathy or optic atrophy with an ophthalmic neuroprotector said method comprising administering to the person in need of such treatment an ophthalmic composition comprising ramipril or ramiprilate and a pharmaceutically acceptable vehicle is yet another aspect of the invention described herein.

The optic neuropathy or optic atrophy that can be treated is congenital optic atrophy, ischemic optic neuropathy, inflammatory optic neuropathy, compressible optic neuropathy, infiltrative optic neuropathy, traumatic optic neuropathy, mitochondrial optic neuropathy, nutritional optic neuropathy, toxic optic neuropathy, hereditary optic neuropathy, Leber's hereditary optic neuropathy, congenial optic atrophy, autosomal dominant optic atrophy, type Kjer or inclusion of the central artery in the eye.

In yet another aspect the optic neuropathy is toxic optic neuropathy due to acute methanol poisoning or ischemic optic neuropathy or inflammatory optic neuropathy, such as optic neuritis, neuromyelitis optica or sarcoidosis.

The ophthalmic composition, as described herein can be used in the method in the form of a solid or a solution and can be administered orally, parentally, intravenously, intramuscularly, topically or by intra-ocular injection. It can also be administered as eye drops.

In yet another embodiment the present invention provides a method to maintain or ameliorate the visual function the visual function of a person in need of such treatment, said method comprising administering to the person in need of such treatment an ophthalmic composition comprising at least one angiotensin converting enzyme (ACE) inhibitor and a pharmaceutically acceptable vehicle.

In yet another embodiment the present invention provides a method to maintain or ameliorate the visual function the visual function of a person in need of such treatment, said method comprising administering to the person in need of such treatment an ophthalmic composition comprising ramipril or ramiprilate and a pharmaceutically acceptable vehicle.

The visual function is visual acuity or visual field.

DESCRIPTION OF THE PREFERRED EMBODIMENTS

Figure 1:
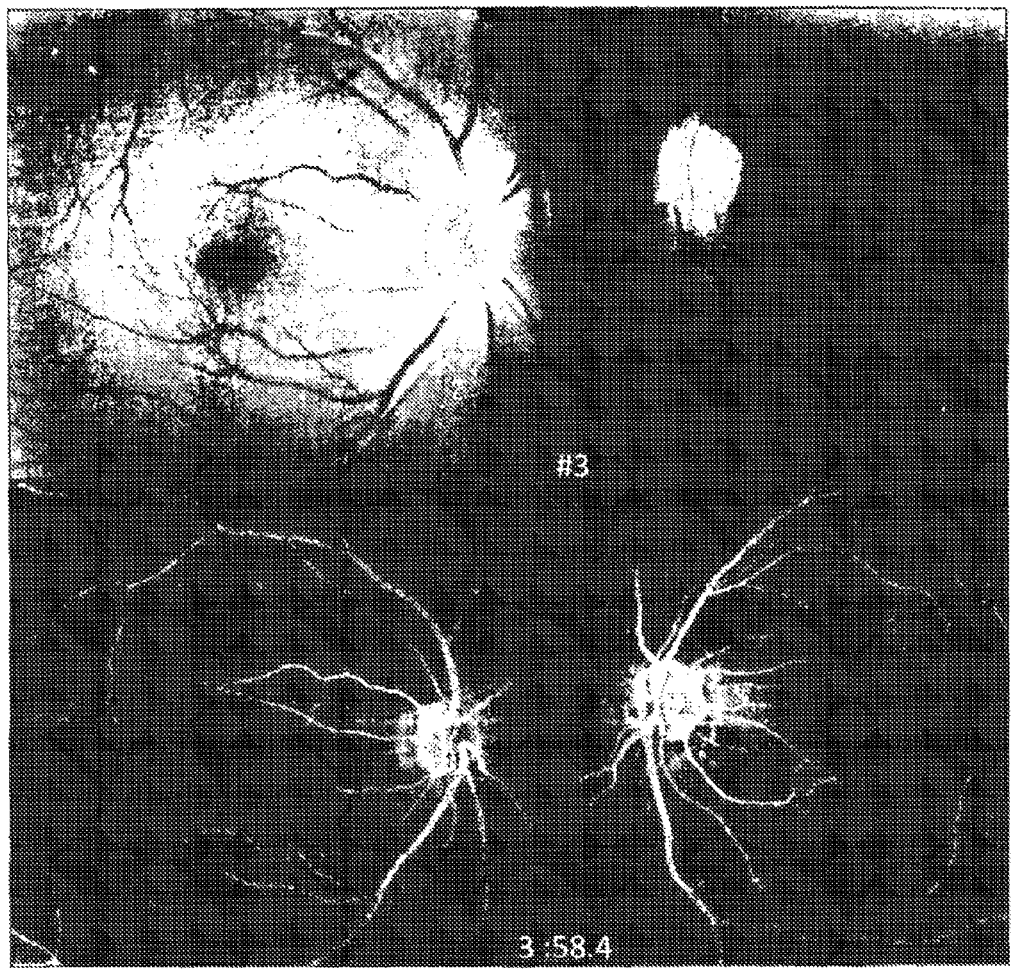
FIG. 1 is a fluoangiography of patient RW, who has Leber's optic neuropathy.

As used herein, the term "ophthalmic neuroprotector" means a ophthalmic composition that can be used in therapy that prevents, retards or reverses apoptosis associated neuronal death resulting from primary neuronal lesions.

"To ameliorate the visual function" means that the vision of an individual is improved from its initial state.

"ACE inhibitors", as used herein, is the abbreviation for angiotensin converting enzymes inhibitors, which block the conversion of angiotensin I to angiotensin II. ACE inhibitors also dilate blood vessels. They are known for use in patients with hypertension and congestive heart failure. ACE inhibitors, as described herein, encompass fosinopril, ramipril, captopril, trandolapril, moexipril, lisinopril, quinapril, enalapril, lisinopril, perindopril, benazepril and mixtures thereof, as well as their active metabolites.

The term "methanol", as used herein, includes methyl alcohol and wood alcohol.

The terms "treating" and "treatment" mean that the eye disorder and/or eye disease is improved.

"Consisting essentially of" as used herein means that the ophthalmic composition can have the ACE inhibitors as their main active principle and pharmaceutically acceptable vehicles, as well as additional ingredients that have do not interfere with the activity of the pharmaceutically active principle.

The present invention concerns the use of medications destined for the treatment of ophthalmic diseases for obtaining an improvement in visual function and, in particular, visual field and visual acuity in patients suffering from optic neuropathies. These optic neuropathies, for example, include Leber's hereditary optic neuropathy, congenial optic neuropathy or deterioration of the optic nerve involving vascular factors. A number of the pathologies are involved and some of which are mentioned below include, for example, (1) Leber's hereditary optic neuropathy, (2) congenial optic atrophy and (3) ischemic and/or inflammatory optic neuropathies.

The molecules that are most efficient to treat these ophthalmic diseases are rampiril, that has the formula:

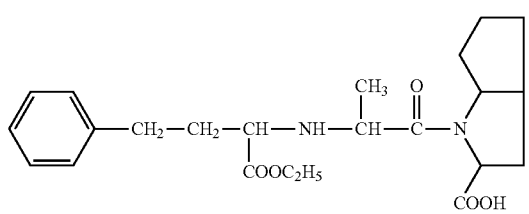

or ramprilat, which is the result of the deesterification of rampiril having the formula;

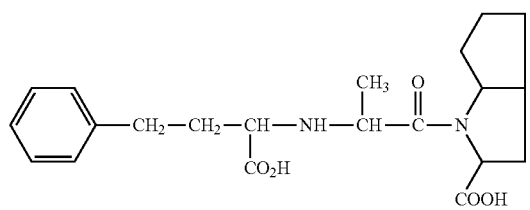 [SMILES: CC(NC(CCc1ccccc1)C(=O)O)C(=O)N1C(C(=O)O)CC2CCCC21]

Without doubt these medications intervene in the mechanism of action of angiotems inconverting enzyme inhibitors (ACE) in the measure where they act to prevent the transformation of angiotensin I to angiotensin II, which are vasoconstrictors and degrade brandykinins, which are vasodialators. These angiotensin converting enzyme inhibitors thus leads to vasodialation that has an effect also on the arteries and veins and is known as mixed vasodialators.

It is also possible to use in place of rampiril or rampirilate all other angiotensin converting enzyme inhibitors (ACE) that have a characteristic of being lipophilic (but may also, if necessary, conserve a character rather hydrophilic), these angiotensin converting enzyme inhibitors (ACE) presents an important affinity for the enzyme's conversion and therefore form stable enzyme-inhibitor complexes.

Thus the present invention provides an ophthalmic composition comprising at least one angiotensin converting enzyme (ACE) inhibitor and a pharmaceutically acceptable vehicle for use as an ophthalmic neuroprotector for treating an optic neuropathy or optic atrophy.

The ACE inhibitors that can be used in the ophthalmic compositions, described herein, include fosinopril, ramipril, captopril, trandolapril, moexipril, lisinopril, quinapril, enalapril, perindopril, benazepril and mixtures thereof, as well as their active metabolites.

The active metabolites of ACE inhibitors include fosinoprilate, ramiprilate, trandolaprilate, moexiprilate, quinaprilate, enalaprilate, perindoprilate and benazeprilate. Captopril and linsinopril are the only ACE inhibitors that are not prodrugs.

In one aspect, the ACE inhibitors that are lipophilic are, in order of increasing lipophilicity, fosinopril, peridopril, moexipril quinapril, benazepril, ramipril, enalapril, captopril and lisinopril.

In another embodiment an ophthalmic composition comprising ramipril or ramiprilate and a pharmaceutically acceptable vehicle for use as an ophthalmic neuroprotector for treating an optic neuropathy or optic atrophy is provided by the present invention.

Examples of optic neuropathies or optic atrophies that can be treated with the ophthalmic compositions, as described herein, include congenital optic atrophy, ischemic optic neuropathy, inflammatory optic neuropathy, compressible optic neuropathy, infiltrative optic neuropathy, traumatic optic neuropathy, mitochondrial optic neuropathy, nutritional optic neuropathy, toxic optic neuropathy and hereditary optic neuropathy.

In another aspect the optic neuropathy is toxic optic neuropathy due to acute methanol poisoning or ischemic optic neuropathy or inflammatory optic neuropathy or inclusion of the central artery in the eye.

Methanol poisoning comes from ingesting methyl alcohol or wood alcohol. The primary site of ocular injury from ingesting methanol is the optic nerve head and intraorbital portion of the optic nerve rather than the retinal ganglia. The initial symptoms are visual disturbances; i.e., the vision is indistinct and it is described like "being in a snow storm."

Examples of inflammatory optic neuropathy include optic neuritis, neuromyelitis optica and sarcoidosis.

The hereditary optic neuropathies that can be treated with the ophthalmic compositions, described herein, include Leber's hereditary optic neuropathy, congenital optic atrophy and autosomal dominant optic atrophy, type Kjer.

In another aspect the present invention provides an ophthalmic composition comprising ramipril or ramiprilate and a pharmaceutically acceptable vehicle for use as an ophthalmic neuroprotector to maintain or ameliorate the visual function of a person in need of such treatment. In many instances, for example, in hereditary optic neuropathies, as described herein, to just maintain the visual function of a patient at the onset of the neuropathy is an accomplishment. Although the visual function may be slightly impaired when the visual function is maintained, it does not deteriorate through the course of life.

Besides maintaining the vision of the patient, the ophthalmic compositions, as described herein, can ameliorate the patient's vision. In this regard, the vision gets clearer due to the treatment.

By visual function is meant visual acuity or visual field. Visual acuity is the clarify or sharpness of vision, which depends on the sharpness of the retinal focus within the eye. A classic Snellen chart is used to test visual acuity. Normal visual acuity is referred to as 20/20 vision, the metric value being 6/6 vision. The first number refers to the distance at which the patient's vision is tested, which is general 20 feet or 6 meters. The second number indicates the distance in which a normal eye can see the symbol or letter on the chart.

Visual field is determined through visual field testing the full horizontal and vertical range of what a patient is able to see peripherally. This type of testing is usually performed with an automated perimetry test in which the patient stares at a source of light straight ahead and random lights of different densities are flashed in their peripheral field of vision. The patient presses a button or other means to indicate that they can see the light.

A method for treating optic neuropathies or optic atrophies, as described herein, with an ophthalmic neuroprotector said method comprising administering to the person in need of such treatment an ophthalmic composition comprising at least one ACE inhibitor and a pharmaceutically acceptable vehicle, is yet another aspect of the present invention.

The ACE inhibitors can be fosinopril, ramipril, captopril, trandolapril, moexipril, lisinopril, quinapril, enalapril, perindopril, benazepril and mixtures thereof, as well as their active metabolites.

In one aspect, the ACE inhibitors that are lipophilic are, in order of lipophilicity, fosinopril, peridopril, moexipril quinapril, benazepril, ramipril, enalapril, captopril and lisinopril.

In another aspect ramipril or ramiprilate and a pharmaceutical acceptable vehicle is used in the ophthalmic composition in the method to treat optic neuropathies, described herein.

A method to maintain or ameliorate the visual function of a person in need of such treatment, said method comprising administering to the person in need of such treatment an ophthalmic composition comprising at least one angiotension converting enzyme inhibitor (ACE) and a pharmaceutically acceptable vehicle. The ACE inhibitors can be fosinopril, ramipril, captopril, trandolapril, moexipril, lisinopril, quinapril, enalapril, perindopril, benazepril and mixtures thereof, as well as their active metabolites.

The pharmaceutically acceptable vehicle can be any acceptable carrier, adjuvant or vehicle that does not interfere with the pharmaceutical activity of the opthalmic composition and is not toxic to the host to which the composition is administered. It includes solvents, dispersion media, coatings, absorption delaying agents and the like. These pharmaceutically acceptable vehicles are described in Remington's Pharmaceutical Sciences 21st edition 2006. An acceptable vehicler can be, for example, saline, buffered saline and the like. It can be added to the pharmaceutical composition after its formulation.

The ophthalmic composition can be in the form of a solid or a solution. It can be a compressed tablet or a solution in the form of eye drops. The ophthalmic composition can be administered orally, parentally, intravenously, intramuscularly, topically or by intra-ocular injection.

In one aspect the ophthalmic composition is administered topically in the form of eye drops.

The effective amount of a ACE inhibitor for treating optic neuropathies of the eye is generally administered to a person or an animal in need thereof in a concentration ranging from 0.001 to 15% (w/v), preferably from 0.05 to 10% (w/v), and more preferably from 0.1 to 3% (w/v).

A kit is another aspect of the present invention comprising, consisting or consisting essentially of:
a) at least one ACE inhibitor selected from the group of: fosinopril, ramipril, captopril, trandolapril, moexipril, lisinopril, quinapril, enalapril, perindopril, benazepril and mixtures thereof, as well as their active metabolites in the doses as described herein; and
b) a pharmaceutically acceptable vehicle, as described herein.

Directions for use can also be added to the kit.

In particular, this invention concerns the use of the products described herein for the fabrication of medicaments that can be used to treat people to improve their visual acuity and visual field.

The invention concerns also pharmaceutical compositions in which the active principal is combined with pharmaceutically acceptable vehicles permitting its administration through different forms such as orally, parenterally, intravenously, intermuscularly, transdermically and topically. The pharmaceutical compositions can be formulated as eye drops, ointments and intraocular injections. Preferably in topical form such as eye drops, ointments and intraocular injections.

EXAMPLES

Example 1

Leber's Hereditary Optic Neuropathy

Leber's hereditary optic neuropathy is a genetic disease that typically starts by a gradual painless and bilateral decrease in vision in young patients. This disease affects both males and females. Females are affected in a less serious way. The first sign of this disease is a visual blurring affecting the central visual field. The disease is bilaterial in 75% of the cases. An improvement often occurs after the acute phase then a progressive loss of vision and the visual field testing shows a large central scotoma, rendering the patient legally blind. The fundus exam reveals peripapillary telangiectasia, a microangiopathy, a pseudo-edema and vascular tortuosity. The study of the electrophysiology of the optic nerve confirms the primary involvement thereof and eliminates retinal pathology. In absence of family history of Leber's optic neuropathy, brain imaging is necessary to eliminate a possible tumor responsible for optic antrophy. In the genome more than 95% of individuals have a mitochondrial DNA anomaly that is detected. The mode of transmission of mitochondrial defects and penetrance varies based on the sex and age of the person. Leber's hereditary optic neuropathy is only transmitted through the mother. However, males never transmit this disease, but a female can transmit it to all descendents.

Patients

Figure 2:
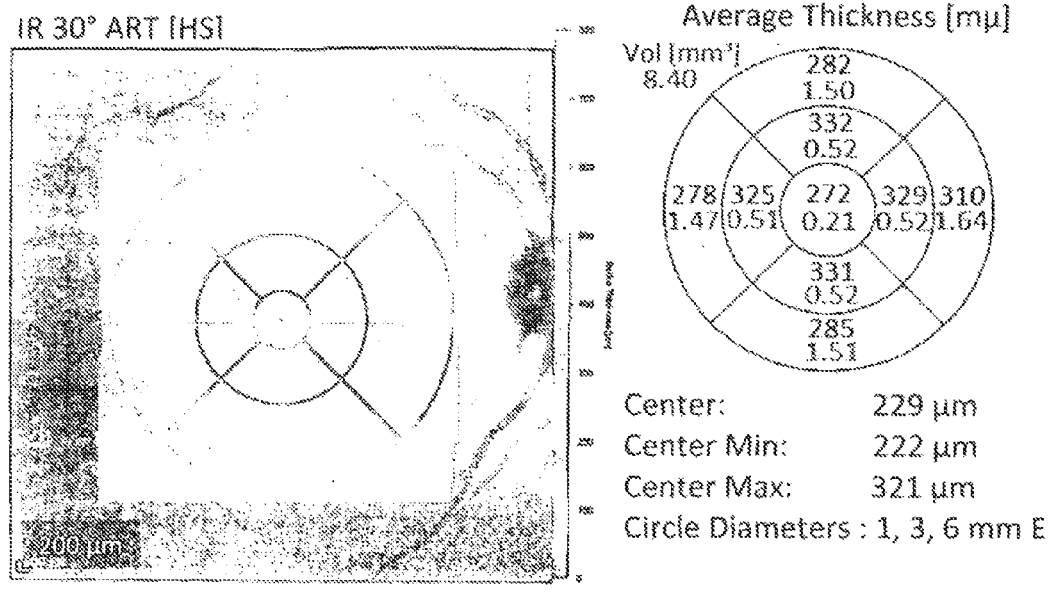
FIG. 2 is an optical coherence tomography scan (OCT) of patient RW, who has Leber's optic neuropathy.
Figure 2:
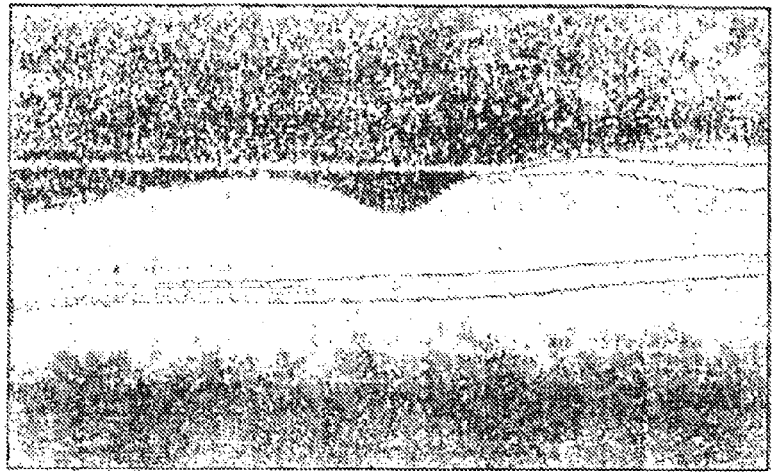

Patient RW has Leber's optic neuropathy with a visual acuity of 1/20 in the right eye and zero in the left eye prior to treatment. A fluoangiography of patient RW, measured before treatment is shown in FIG. 1. An optical coherence tomography scan of patient RW is shown in FIG. 2 before treatment.

An intraocular injection (intravitreal) of 2% (w/v) ramiprilate in a quantify of 0.1 to 0.2 ml, which was injected once every 15 days for a total of three injections. The visual acuity was measured after this treatment. The results of 2/10 in the right eye and 1/20 in the left eye were achieved, Patient CL has Leber's optic neuropathy and had only bright perceptions in two eyes. Visual acuity was measured prior to treatment.

An intraocular injection (intravitreal) of 2% (w/v) ramiprilate in a quantity of 0.1 to 0.2 ml, which was infected once every 15 days for a total of three injections. The visual acuity was measured after this treatment. The visual acuity was 2/10 for both eyes.

Example 2

Anterior Optic Neuropathic Ischemia

Figure 3:
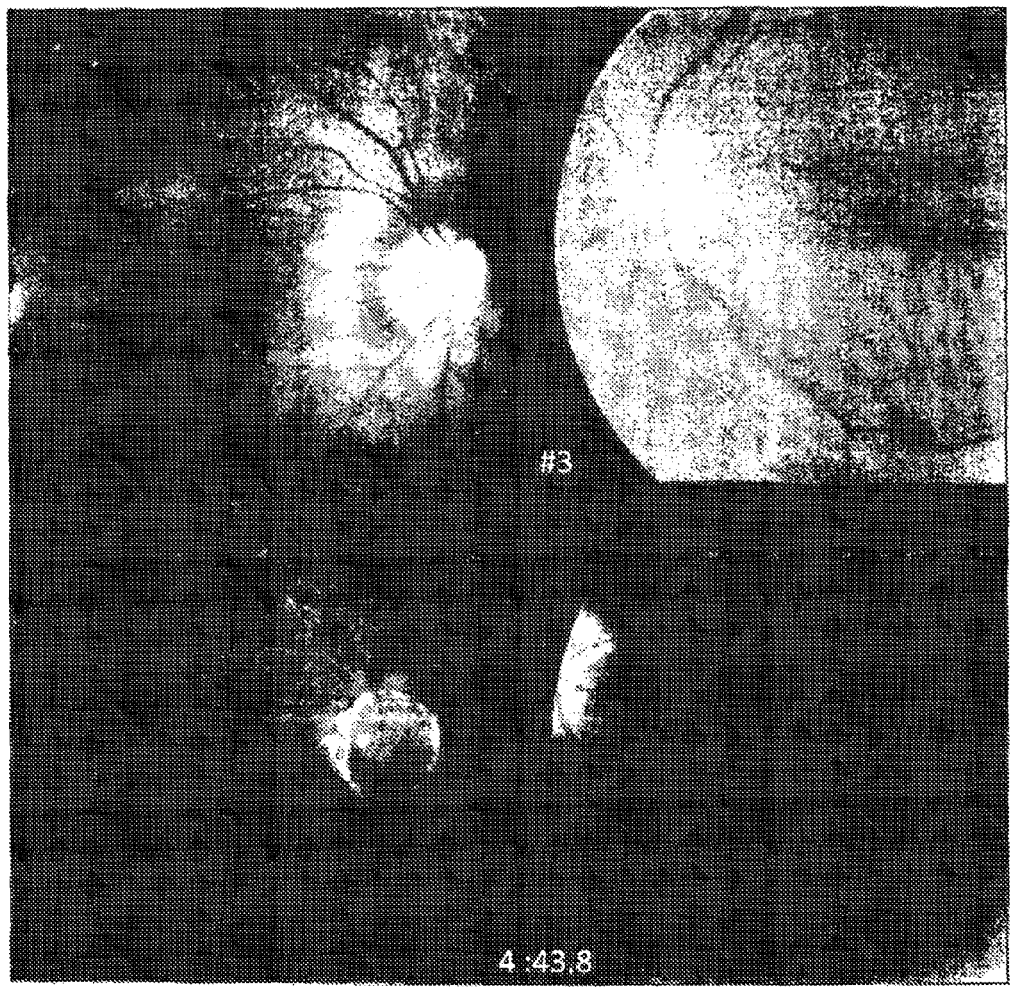
FIG. 3 is a fluoangiography of patient MM, who has anterior optic neuropathy ischemia.
Figure 4:
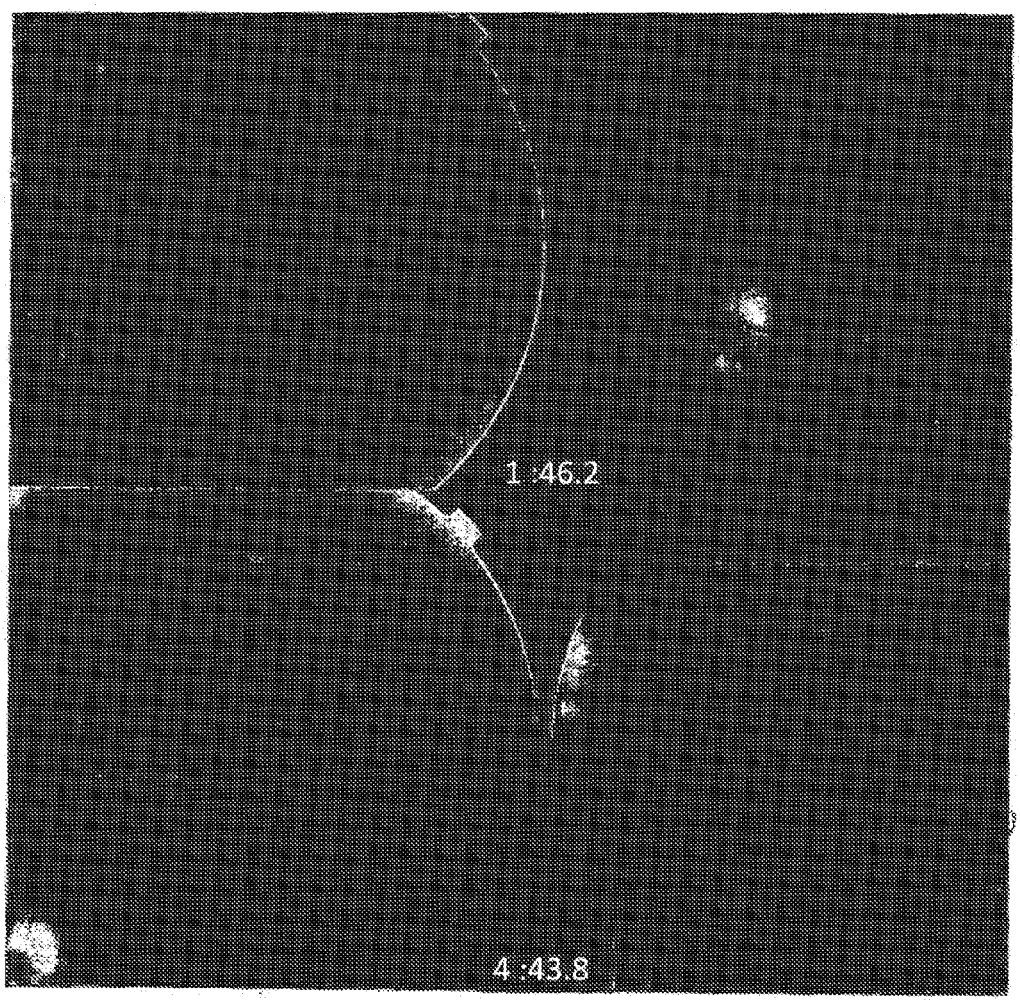
FIG. 4 is a fluoangiography of patient MM, who has anterior optic neuropathy ischemia.

Patient MM has bilateral asymmetric anterior optic neuropathy ischemia and had a visual acuity of 1/10 in both eyes, prior to treatment. FIGS. 3 and 4 show a fluoangiography of MM before treatment.

MM was administered an intravitreal injection of 2% (w/v) ramiprilate in a quantify of 0.1 to 0.2 ml, which was injected once every 15 days for a total of three injections. The visual acuity was then taken and was 5/10 for both eyes.

Example 3

Dominant and Recessive Congenital Optic Atrophy 2 patients that have dominant recessive congenital optic atrophy had bad visual acuity.

These 2 patients were treated with eye drops containing 2% (w/v) ramiprilate 2 times per day for a duration of 3 months. Their vision was greatly improved as indicated by an improvement in visual acuity.

Example 4

Figure 5:
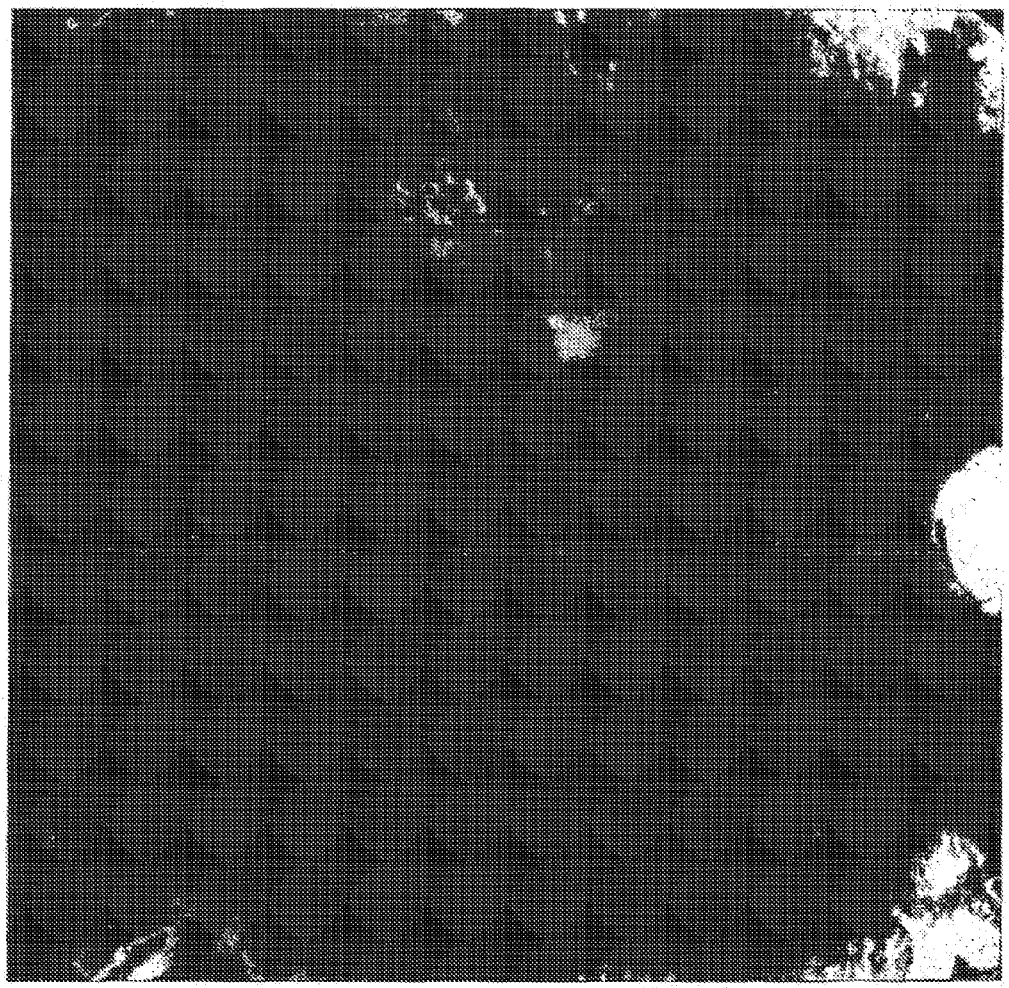
FIG. 5 is a fundus photograph of patient ST, who has central artery occlusion.

Central Retinal Artery Occlusion of the Retina 2 patients (ST and VV) suffering from central artery occlusion of the retina had had visual acuity. FIG. 5 is a fundus photograph of patient ST before treatment.

One was administered 2% (w/v) ramprilate in an eye drop formulation twice a day for 3 months, while the other was administered 2% (w/v) ramprilate in via an intravitreal injection ramiprilate in a quantity of 0.1 to 0.2 ml, which was injected once every 15 days for a total of three injections. Both patients had an improvement in vision as indicated by an improvement in visual acuity.

Example 5

Figure 6:
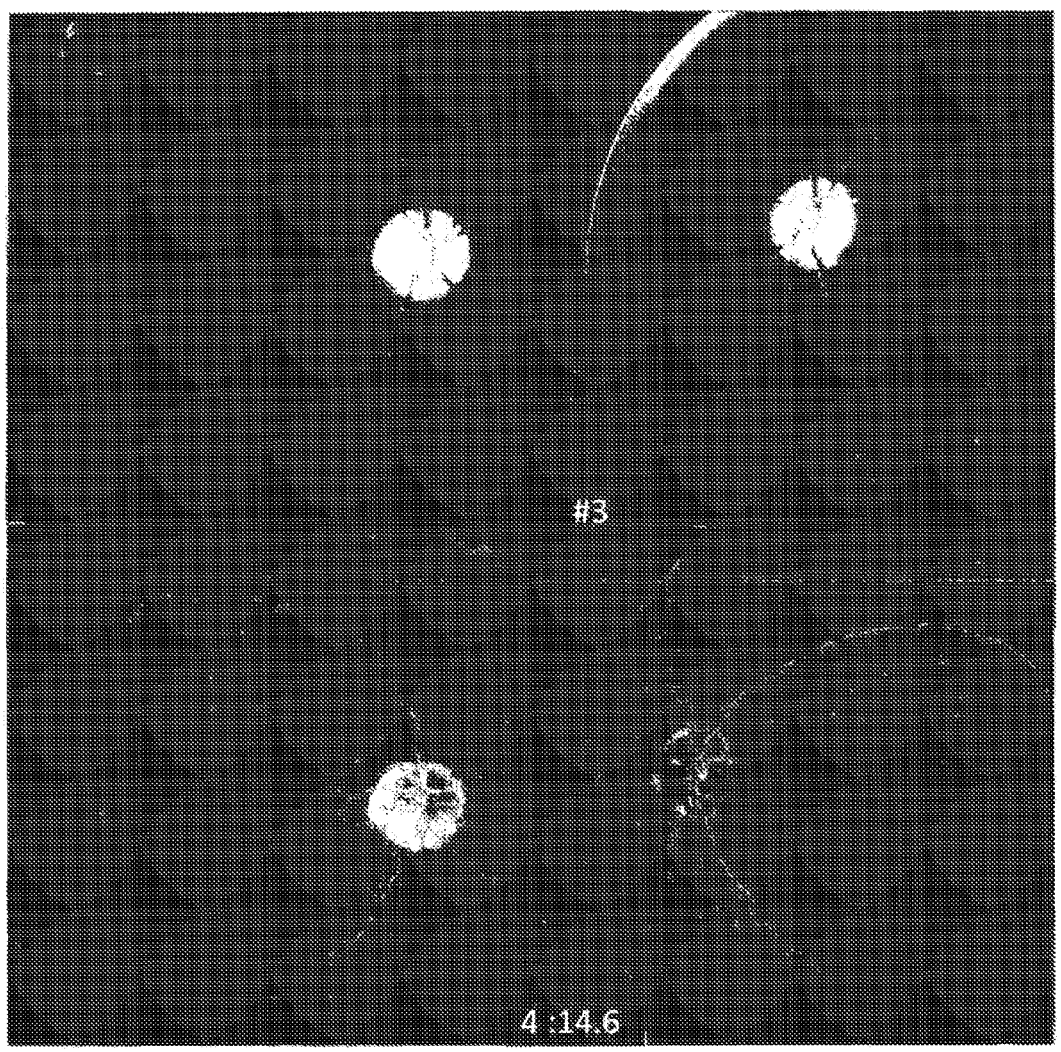
FIG. 6 is a fluoangiography of patient SR, who suffers from toxication due to ingestion of methyl alcohol.
Figure 7:
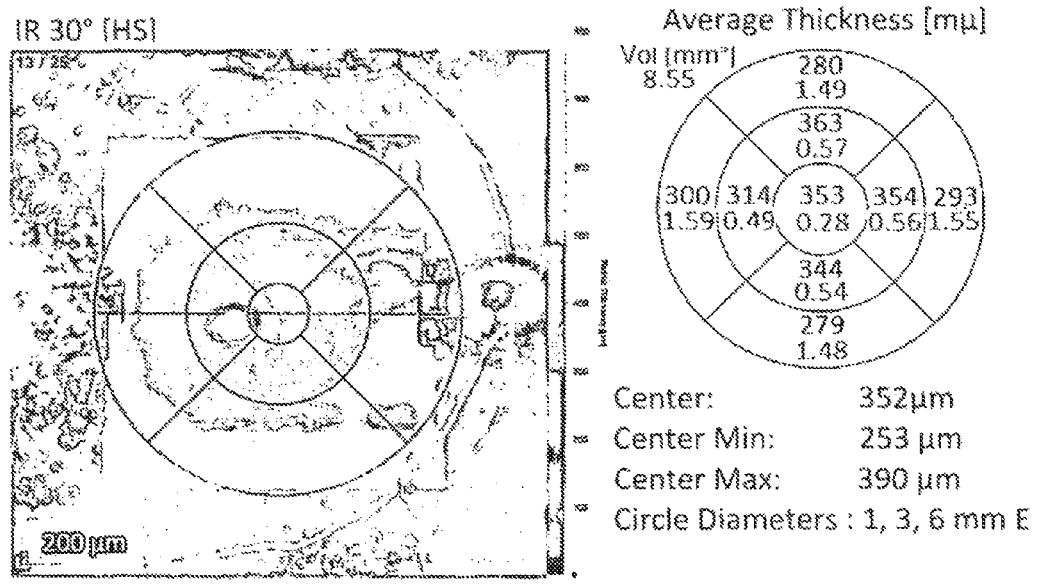
FIG. 7 is an optical coherence tomography (OCT) scan of patient SR, who suffers from toxication due to ingestion of methyl alcohol.
Figure 7:

Toxication by Ingestion of Methyl Alcohol 2 patients (SR and WW) suffering from toxication by ingestion of methyl alcohol has bad visual acuity. FIG. 6 is a fluoangiography of SR prior to treatment. FIG. 7 is an optical coherence tomography scan of SR before treatment.

One patient was administered 2% (w/v) ramprilate in an eye drop formulation twice a day for 3 months, while the other patient was administered 2% (w/v) ramprilate in via an intravitreal injection ramiprilate in a quantity of 0.1 to 0.2 ml, which was injected once every 15 days for a total of three injections. Both patients had an improvement in vision as indicated by improved visual acuity Example 6

Other ACE Inhibitors

Fosinoprilate, trandolaprilate, moexiprilate, quinaprilate, enalaprilate, perindoprilate and benazeprilate, as well as captopril and lisinopril are also tested in patients having the same optic neuropathy or congenital optic atrophy as in Examples 1 to 5 using similar procedures. Similar results of improvement in visual acuity are achieved.

What is claimed is:

1. A method for treating an optic neuropathy, which is an hereditary or inflammatory optic neuropathy with an ophthalmic neuroprotector said method comprising administering to a person in need of such treatment an ophthalmic composition comprising at least one angiotensin converting enzyme (ACE) inhibitor and a pharmaceutically acceptable vehicle, wherein:
   (i) the hereditary optic neuropathy is selected from the group consisting of Leber's hereditary optic neuropathy, congenial optic atrophy and autosomal dominant optic atrophy, type Kjer, or
   (ii) the inflammatory optic neuropathy is selected from the group consisting of optic neuritis, neuromyelitis optica and sarcoidosis, or
   (iii) both (i) and (ii).

2. The method according to claim 1, wherein said at least one angiotensin converting enzyme (ACE) inhibitor is fosinopril, ramipril, captopril, trandolapril, moexipril, lisinopril, quinapril, enalapril, perindopril, benazepril and mixtures thereof.

3. The method according to claim 1, wherein said at least one angiotensin converting enzyme (ACE) inhibitor is fosinoprilate, trandolaprilate, moexiprilate, ramiprilate, quinaprilate, enalaprilate, perindoprilate and benazeprilate.

4. The method according to claim 1, wherein said at least one angiotensin converting enzyme (ACE) inhibitor is an active metabolite of fosinopril, ramipril, captopril, trandolapril, moexipril, lisinopril, quinapril, enalapril, perindopril, benazepril and mixtures thereof.

5. The method according to claim 1, wherein the optic neuropathy being treated is a hereditary optic neuropathy selected from the group consisting of Leber's hereditary optic neuropathy, congenial optic atrophy and autosomal dominant optic atrophy, type Kjer.

6. The method according to claim 1, wherein the optic neuropathy being treated is a inflammatory optic neuropathy selected from the group consisting of optic neuritis, neuromyelitis optica and sarcoidosis.

7. The method according to claim 1, wherein said ophthalmic composition is in the form of a solid or a solution.

8. The method according to claim 1, wherein said ophthalmic composition can be administered orally, parentally, intravenously, intramuscularly, topically or by intra-ocular injection.

9. The method according to claim 8, wherein said topically administration is by eye drops.

10. The method according to claim 1, wherein the angiotensin converting enzyme (ACE) inhibitor is administered to a person in need of such treatment in a concentration ranging from 0.001 to 15% (w/v).

11. The method according to claim 10, wherein the angiotensin converting enzyme (ACE) inhibitor is administered to a person in need of such treatment in a concentration ranging from 0.05 to 10% (w/v).

12. The method according to claim 11, wherein the angiotensin converting enzyme (ACE) inhibitor is administered to a person in need of such treatment in a concentration ranging from 0.1 to 3% (w/v).

13. The method according to claim 1, wherein the angiotensin converting enzyme (ACE) inhibitor is ramiprilate and is administered by intra-ocular injection to a person in need of such treatment in a concentration of 2% (w/v) in a quantity of 0.1 to 0.2 ml.

\* \* \* \* \*